(12) United States Patent
Itoh et al.

(10) Patent No.: US 6,838,445 B1
(45) Date of Patent: Jan. 4, 2005

(54) TUMOR ANTIGEN PEPTIDE ORIGINATING IN SART-1

(75) Inventors: Kyogo Itoh, Saga (JP); Masanobu Nakao, Okawa (JP)

(73) Assignee: Kyogo Itoh, Saga (JP)

( * ) Notice: Subject to any disclaimer, the term of this patent is extended or adjusted under 35 U.S.C. 154(b) by 0 days.

(21) Appl. No.: 09/743,467

(22) PCT Filed: Jul. 7, 1999

(86) PCT No.: PCT/JP99/03659
§ 371 (c)(1),
(2), (4) Date: Jan. 10, 2001

(87) PCT Pub. No.: WO00/02907
PCT Pub. Date: Jan. 20, 2000

(30) Foreign Application Priority Data

Jul. 10, 1998 (JP) ............................................ 10/196152

(51) Int. Cl.⁷ ............................ A61K 48/00; C07K 7/06
(52) U.S. Cl. .................... 514/44; 530/300; 530/328; 536/23.1; 536/23.5; 435/320.1
(58) Field of Search ............... 514/44, 2.29; 424/277.1; 530/328, 300; 425/320.1; 536/23.1

(56) References Cited

FOREIGN PATENT DOCUMENTS

| WO | A1-9929715 | | 6/1996 |
| WO | WO 97/34617 | * | 3/1997 |
| WO | A1-9746676 | | 12/1997 |

OTHER PUBLICATIONS

Gouttefangeas C. et al. Problem solving for tumor immunotherpay. Nature Biotech vol. 18, pp. 491–492; 2000.*
Dalgleish A.G. Current problems in the development of specific immunotherapeutic approaches to cancer. Journ. Clinical Path. vol. 54, pp. 675–676; 2001.*
Shichijo et al., J. Exp. Med., vol. 187, No. 3, pp. 277–288 (1998).
Nakao et al., Cancer Res., vol. 55, No. 19, pp. 4248–52 (1995).
Rivoltini et al., J. Immunol., vol. 154, No. 5, pp. 2257–65 (1995).
Rammensee et al., Immunogenetics, vol. 41, No. 4, pp. 178–228 (1995).
Kubo et al., J. Immunol., vol. 152, No. 8, pp. 3913–24 (1994).
Kondo et al., J. Immunol., vol. 155, No. 9, pp. 4307–12 (1995).
Kikuchi et al., Int. J. Cancer, vol. 81, No. 3, pp. 459–66 (1999).

* cited by examiner

Primary Examiner—Dave T. Nguyen
Assistant Examiner—Jon Eric Angell
(74) Attorney, Agent, or Firm—Birch, Stewart, Kolasch & Birch, LLP

(57) ABSTRACT

To provide a tumor antigen peptide derived from SART-1 and a derivative thereof, possessing functionally equivalent characteristics thereto; or a therapeutic agent, prophylactic agent or the like for a tumor, each utilizing, the tumor antigen peptide.

6 Claims, 1 Drawing Sheet

SEQUENCE LISTING

<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Ala Phe Arg Gln Leu Ser His Arg Phe
                 5

<210> SEQ ID NO 2
<211> LENGTH: 11
<212> TYPE: PRT
<213> ORGANISM: Homo sapiens

<400> SEQUENCE: 2

Lys Met Lys Thr Glu Arg Arg Met Lys Lys Leu
                 5                  10

<210> SEQ ID NO 3
<211> LENGTH: 10
<212> TYPE: PRT
<213> ORGANISM: Homo sapiens

<400> SEQUENCE: 3

Arg Met Lys Lys Leu Asp Glu Glu Ala Leu
                 5                  10

<210> SEQ ID NO 4
<211> LENGTH: 11
<212> TYPE: PRT
<213> ORGANISM: Homo sapiens

<400> SEQUENCE: 4

Arg Met Lys Lys Leu Asp Glu Glu Ala Leu Leu
                 5                  10

<210> SEQ ID NO 5
<211> LENGTH: 9
<212> TYPE: PRT
<213> ORGANISM: Homo sapiens

<400> SEQUENCE: 5

Lys Met Ser Ser Ser Asp Thr Pro Leu
                 5

<210> SEQ ID NO 6
<211> LENGTH: 9
<212> TYPE: PRT
<213> ORGANISM: Artificial Sequence
<220> FEATURE:
<223> OTHER INFORMATION: Modified peptide derived from Homo sapiens
<221> NAME/KEY: VARIANT
<222> LOCATION: 2
<223> OTHER INFORMATION: Xaa is Phe, Tyr, Met or Trp.
<221> NAME/KEY: VARIANT
<222> LOCATION: 9
<223> OTHER INFORMATION: Xaa is Phe, Leu, Ile, Trp or Met.

<400> SEQUENCE: 6

Ala Xaa Arg Gln Leu Ser His Arg Xaa
                 5

```
<210> SEQ ID NO 7
<211> LENGTH: 11
<212> TYPE: PRT
<213> ORGANISM: Artificial Sequence
<220> FEATURE:
<223> OTHER INFORMATION: Modified peptide derived from Homo sapiens
<221> NAME/KEY: VARIANT
<222> LOCATION: 2
<223> OTHER INFORMATION: Xaa is Phe, Tyr, Met or Trp.
<221> NAME/KEY: VARIANT
<222> LOCATION: 11
<223> OTHER INFORMATION: Xaa is Phe, Leu, Ile, Trp or Met.

<400> SEQUENCE: 7

Lys Xaa Lys Thr Glu Arg Arg Met Lys Lys Xaa
                5                   10

<210> SEQ ID NO 8
<211> LENGTH: 10
<212> TYPE: PRT
<213> ORGANISM: Artificial Sequence
<220> FEATURE:
<223> OTHER INFORMATION: Modified peptide derived from Homo sapiens
<221> NAME/KEY: VARIANT
<222> LOCATION: 2
<223> OTHER INFORMATION: Xaa is Phe, Tyr, Met or Trp.
<221> NAME/KEY: VARIANT
<222> LOCATION: 10
<223> OTHER INFORMATION: Xaa is Phe, Leu, Ile, Trp or Met.

<400> SEQUENCE: 8

Arg Xaa Lys Lys Leu Asp Glu Glu Ala Xaa
                5                   10

<210> SEQ ID NO 9
<211> LENGTH: 11
<212> TYPE: PRT
<213> ORGANISM: Artificial Sequence
<220> FEATURE:
<223> OTHER INFORMATION: Modified peptide derived from Homo sapiens
<221> NAME/KEY: VARIANT
<222> LOCATION: 2
<223> OTHER INFORMATION: Xaa is Phe, Tyr, Met or Trp.
<221> NAME/KEY: VARIANT
<222> LOCATION: 11
<223> OTHER INFORMATION: Xaa is Phe, Leu, Ile, Trp or Met.

<400> SEQUENCE: 9

Arg Xaa Lys Lys Leu Asp Glu Glu Ala Leu Xaa
                5                   10

<210> SEQ ID NO 10
<211> LENGTH: 9
<212> TYPE: PRT
<213> ORGANISM: Artificial Sequence
<220> FEATURE:
<223> OTHER INFORMATION: Modified peptide derived from Homo sapiens
<221> NAME/KEY: VARIANT
<222> LOCATION: 2
<223> OTHER INFORMATION: Xaa is Phe, Tyr, Met or Trp.
<221> NAME/KEY: VARIANT
<222> LOCATION: 9
<223> OTHER INFORMATION: Xaa is Phe, Leu, Ile, Trp or Met.

<400> SEQUENCE: 10

Lys Xaa Ser Ser Ser Asp Thr Pro Xaa
                5

<210> SEQ ID NO 11
<211> LENGTH: 9
<212> TYPE: PRT
```

```
<213> ORGANISM: Homo sapiens

<400> SEQUENCE: 11

Asp Phe Ser Ala Ser Ser Thr Thr Ile
                5

<210> SEQ ID NO 12
<211> LENGTH: 10
<212> TYPE: PRT
<213> ORGANISM: Homo sapiens

<400> SEQUENCE: 12

Asp Phe Ser Ala Ser Ser Thr Thr Ile Leu
                5                   10

<210> SEQ ID NO 13
<211> LENGTH: 10
<212> TYPE: PRT
<213> ORGANISM: Homo sapiens

<400> SEQUENCE: 13

Val Tyr Cys Ile Glu Asp Lys Met Ala Ile
                5                   10

<210> SEQ ID NO 14
<211> LENGTH: 11
<212> TYPE: PRT
<213> ORGANISM: Homo sapiens

<400> SEQUENCE: 14

Lys Tyr Ser Arg Arg Glu Glu Tyr Arg Gly Phe
                5                   10

<210> SEQ ID NO 15
<211> LENGTH: 8
<212> TYPE: PRT
<213> ORGANISM: Homo sapiens

<400> SEQUENCE: 15

Gly Tyr Lys Pro Asp Val Lys Ile
                5

<210> SEQ ID NO 16
<211> LENGTH: 10
<212> TYPE: PRT
<213> ORGANISM: Homo sapiens

<400> SEQUENCE: 16

Glu Tyr Val Asp Glu Thr Gly Arg Lys Leu
                5                   10

<210> SEQ ID NO 17
<211> LENGTH: 9
<212> TYPE: PRT
<213> ORGANISM: Artificial Sequence
<220> FEATURE:
<223> OTHER INFORMATION: Modified peptide derived from Homo sapiens
<221> NAME/KEY: VARIANT

<400> SEQUENCE: 17

Lys Met Ser Ser Ser Asp Pro Thr Leu
                5
```

US 6,838,445 B1

TUMOR ANTIGEN PEPTIDE ORIGINATING IN SART-1

This application is the national phase under 35 U.S.C. §371 of PCT International Application No. PCT/JP99/03659 which has an International filing date of Jul. 7, 1999, which designated the United States of America.

TECHNICAL FIELD

The present invention relates to a tumor antigen peptide derived from SART-1. More particularly, the present invention relates to a novel tumor antigen peptide derived from SART-1 and a derivative thereof possessing functionally equivalent characteristics thereto, and a therapeutic agent, a prophylactic agent, a diagnostic agent, or the like for a tumor, each utilizing these tumor antigen peptide and a derivative thereof in vivo or in vitro.

BACKGROUND ART

There have been known that immune systems, especially T cells, play an important role in the elimination of tumors by organisms. In fact, infiltration of lymphocytes has been found in human tumor foci, the lymphocytes showing cytotoxic activity against tumor cells (Arch. Surg., 126:200, 1990). Cytotoxic T cell (CTL) which recognizes autologous tumor cell has been relatively easily isolated from melanomas (Immunol. Today, 8:385, 1987, J. Immunol., 138:989, 1987, Int. J. Cancer, 52:52, 1992, and the like). In addition, the significance of T cells in the tumor elimination has been also suggested from the clinical results of a treatment of melanomas by CTL transfer (J. Natl. Cancer. Inst., 86:1159, 1994).

Although it has been unknown for a long period of time as to the molecule to which CTL attacking autologous tumor cell is targeted, the molecule has gradually been elucidated by the recent progress in immunology and molecular biology. In other words, there has been elucidated that CTL attacks autologous tumor cell by recognizing a complex by using a T cell receptor (TCR), the complex being formed between a peptide called "tumor antigen peptide" and thereafter a major histocompatibility complex class I antigen (MHC class I antigen; in the case of human, it is referred to as HLA antigen).

Tumor antigen peptides are generated by intracellularly synthesizing an inherent protein in a tumor, i.e. a tumor antigen protein, and thereafter intracellularly degrading by proteasome. The generated tumor antigen peptide binds to MHC class I antigen (HLA antigen) in the endoplasmic reticulum, thereby forming a complex, and the formed complex is transported to cell surface, to thereby be antigen-presented. The antigen-presented complex is recognized by tumor-specific CTL to thereby exhibit anti-tumor effects through cytotoxic actions and production of lymphokines. As a series of actions have been elucidated as described above, a treatment for enhancing tumor-specific CTL in the body of a tumor patient can be accomplished by utilizing a tumor antigen protein or tumor antigen peptide as a so-called cancer vaccine.

As the tumor antigen protein, a protein named MAGE was firstly identified from human melanoma cell by T. Boon et al. in 1991 (Science, 254:1643, 1991). Thereafter, some tumor antigen proteins have been identified mainly from melanoma cell. As the melanoma antigen, there have been identified melanosome proteins such as a melanocyte tissue-specific protein gp100 (J. Exp. Med., 179:1005, 1994), MART-1 (Proc. Natl. Acad. Sci. USA, 91:3515, 1994), and tyrosinase (J. Exp. Med., 178:489, 1993); MAGE-associated proteins expressed in not only melanoma cells but also various kinds of cancer cells and normal testis cell (J. Exp. Med., 179:921, 1994); β-catenin possessing tumor-specific amino acid mutations (J. Exp. Med., 183:1185, 1996); CDK4 (Science, 269:1281, 1995), and the like. In addition, as tumor antigen proteins other than melanomas, there have been identified oncogene products such as HER2/neu (J. Exp. Med., 181:2109, 1995) and p53 (mutant) (Proc. Natl. Acad. Sci. USA, 93:14704, 1996); tumor markers such as CEA (J. Natl. Cancer. Inst., 87:982, 1995) and PSA (J. Natl. Cancer. Inst., 89:293, 1997); viral proteins such as HPV (J. Immunol., 154:5934, 1995) and EBV (Int. Immunol., 7:653, 1995), and the like. These tumor antigen proteins are detailed in the description of review (Immunol. Today, 18:267, 1997; J. Exp. Med., 183:725, 1996; Curr. Opin. Immunol., 8:628, 1996, and the like).

For the purpose of the application of a tumor antigen protein or tumor antigen peptide to the treatment or diagnosis for a tumor, it is important to identify a tumor antigen which can be applied in a wide range to squamous cell carcinomas (esophageal cancer, lung cancer and the like) of which occurrence is outnumbered in frequency as compared to that of melanomas. Regarding to the above, the present inventors have tried to clone a gene encoding a tumor antigen protein from squamous carcinoma cells derived from esophageal cancer. As a result, the present inventors have succeeded in cloning a gene encoding a novel tumor antigen protein (SART-1) for the first time from tumor cells other than melanomas, and identified from SART-1 some of the tumor antigen peptide portions of which are presented by binding with HLA-A26 or the like (J. Exp. Med., 187:277, 1998; WO 97/46676).

When these tumor antigen peptides are actually applied for a clinical test, it is desirable to use plural kinds of heterologous tumor antigen peptides as well as a single kind of tumor antigen peptide. In other words, not all cancer cells necessarily express commonly the same tumor antigen. Rather, in consideration of the fact that two or more kinds of heterologous tumor antigen peptides are presented on a single cancer cell, it is thought that a treatment using plural heterologous tumor antigen peptides is more effective. In fact, since an effect was insufficient with a peptide derived from a single tumor antigen for melanoma, the development of a cocktail preparation comprising plural peptides has been tried (Int. J. Cancer, 66:162, 1996; Int. J. Cancer, 67:54, 1996). In view of the background as described above, there has been desired identification of a novel tumor antigen peptide which can be widely applied to squamous cell carcinoma or the like occurring at high frequency.

An object of the present invention is to provide a tumor antigen peptide derived from SART-1. Concretely, an object of the present invention is to provide a tumor antigen peptide derived from SART-1 and a derivative thereof possessing functionally equivalent characteristic; and a therapeutic agent, a prophylactic agent, a diagnostic agent or the like for a tumor, each utilizing these tumor antigen peptide and a derivative thereof in vivo or in vitro. The tumor antigen peptide derived from SART-1 of the present invention is a tumor antigen peptide presented by binding with an HLA antigen HLA-A24, the HLA-A24 being owned by about 60% of the Japanese population, so that the tumor antigen peptide can be applied to a large number of patients, and the tumor antigen peptide can be also widely applied to squamous cell carcinoma or the like occurring at high frequency. Therefore, the tumor antigen peptide is expected for utility as an anti-tumor agent. In this connection, squamous cell carcinoma is one of cancers most frequently encountered among human cancers. In particular, it has been known that squamous cell carcinoma in esophageal cancer or lung cancer relatively demonstrates resistivities to the current chemotherapy or radiotherapy. From these viewpoints, the development of the tumor antigen peptide of the present invention has been expected.

DISCLOSURE OF INVENTION

As a result of the progress of the studies on the tumor antigen peptide presented by binding with HLA-A24 among the above-mentioned tumor antigen peptides derived from SART-1, the present inventors have elucidated that the peptides of SEQ ID NO: 1 to SEQ ID NO: 5 and the like each possesses an activity as a tumor antigen peptide. The present invention has been perfected thereby.

Specifically, the gist of the present invention relates to:

(1) a tumor antigen peptide comprising all or a part of the amino acid sequence of any one of SEQ ID NO: 1 to SEQ ID NO: 5, wherein the tumor antigen peptide binds to HLA-A24 antigen, thereby allowing to be recognized by cytotoxic T cell, or a derivative thereof possessing functionally equivalent characteristics;

(2) a therapeutic agent or prophylactic agent for a tumor, comprising at least one member selected from the tumor antigen peptide and the derivative thereof of item (1) above as an active ingredient;

(3) a recombinant DNA comprising at least one member of DNAs each encoding the tumor antigen peptide or the derivative thereof of item (1) above;

(4) a polypeptide obtainable by expressing the recombinant DNA of item (3) above;

(5) a therapeutic agent or prophylactic agent for a tumor, comprising the recombinant DNA of item (3) above or the polypeptide of item (4) above as an active ingredient;

(6) an antibody which specifically binds to the tumor antigen peptide or the derivative thereof of item (1) above;

(7) an antigen presenting cell which presents a complex formed between HLA-A24 antigen and the tumor antigen peptide or the derivative thereof of item (1) above on a surface of isolated cells derived from a patient with a tumor, the isolated cells possessing an ability for antigen presentation;

(8) a therapeutic agent for a tumor, comprising the antigen presenting cells of item (7) above as an active ingredient;

(9) a cytotoxic T cell which specifically recognizes a complex formed between HLA-A24 antigen and the tumor antigen peptide or the derivative thereof of item (1) above;

(10) a therapeutic agent for a tumor, comprising the cytotoxic T cell of item (9) above as an active ingredient; and

(11) a diagnostic agent for a tunor, comprising the tumor antigen peptide or the derivative thereof of item (1) above.

BEST MODE FOR CARRYING OUT THE INVENTION

Figure 1:
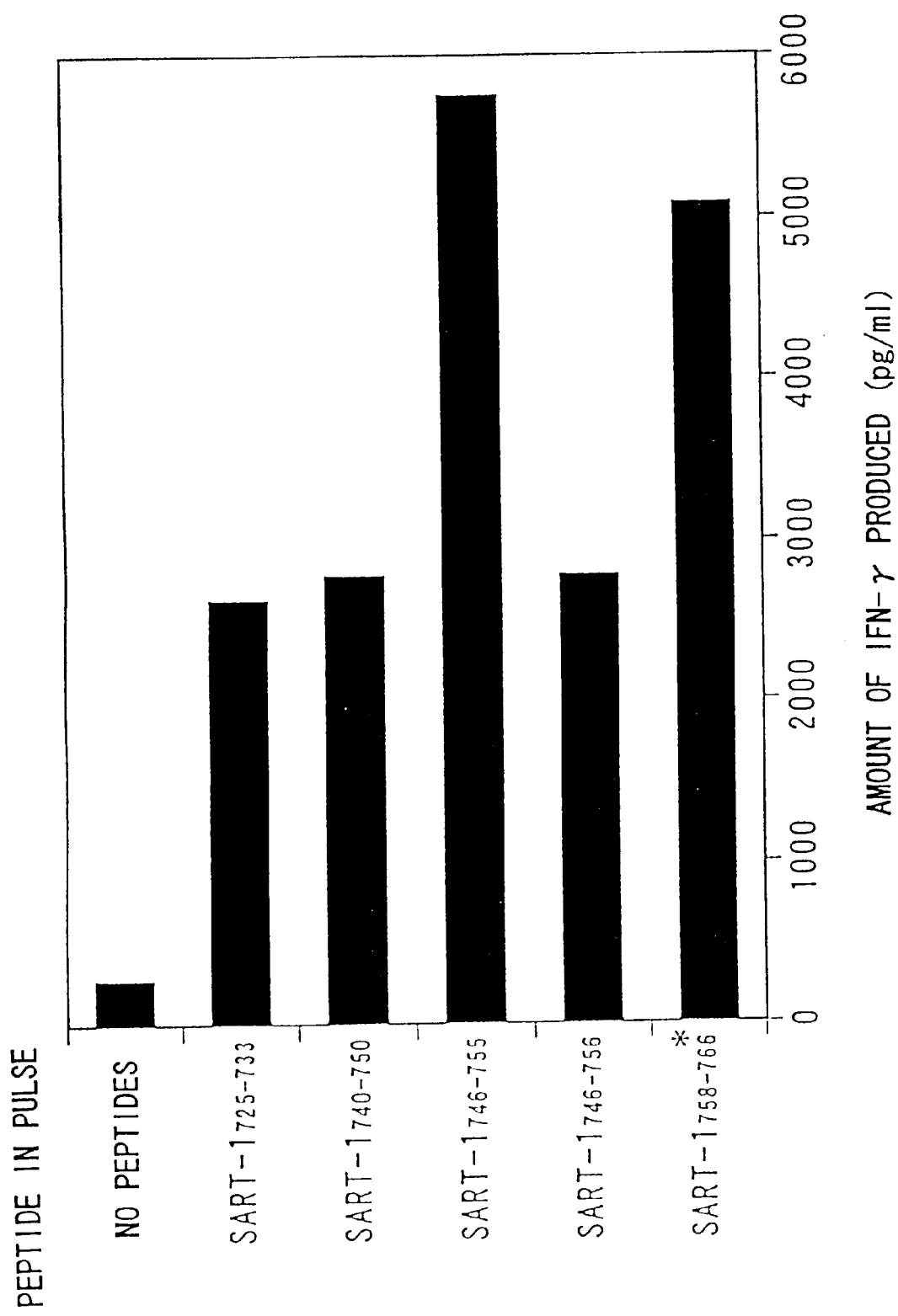
FIG. 1 is a graph showing an amount of IFN-γ produced by KE-4CTL from HLA-A2402-expressing VA-13 cells which present the tumor antigen peptide of the present invention.

The tumor antigen peptide of the present invention refers to a peptide which comprises all or a part of the amino acid sequence of any one of SEQ ID NO: 1 to SEQ ID NO: 5, which is an amino acid sequence derived from SART-1 (described in J. Exp. Med., 187:277, 1998, WO 97/46676), wherein the peptide binds to HLA-A24 antigen, thereby allowing to be recognized by cytotoxic T cell (CTL). In other words, the peptide refers to:

1) a peptide consisting of the amino acid sequence of any one of SEQ ID NO: 1 to SEQ ID NO: 5, or 2) a peptide comprising the amino acid sequence of any one of SEQ ID NO: 1 to SEQ ID NO: 5, the length of which is longer than the amino acid sequence, or a peptide consisting of a part of the amino acid sequence of any one of SEQ ID NO: 1 to SEQ ID NO: 5, wherein the peptide binds to HLA-A24 antigen, thereby allowing to be recognized by CTL.

As preferable examples among the peptides of item 1) above, there are included a tumor antigen peptide consisting of the amino acid sequence of SEQ ID NO: 3, SEQ ID NO: 4, or SEQ ID NO: 5. In addition, as the length of the peptide of item 2) above, there are included those having 8 to 11 amino acids or so.

The peptide mentioned above can be synthesized in accordance with the method used in ordinary peptide chemistry. Methods of synthesis include those described in the publications (*Peptide Synthesis*, Interscience, New York, 1966; *The Proteins*, 2, Academic Press Inc., New York, 1976; *Pepuchido Gosei* (*Peptide Synthesis*), Maruzen, 1975; *Pepuchido Gosei No Kiso To Jikken* (*Fundamental and Experimentation of Peptide Synthesis*), Maruzen, 1985; Iyakuhin No Kaihatsu, Zoku (*Development of Pharmaceuticals, Sequel*), 14, *Pepuchido Gosei* (*Peptide Synthesis*), Hirokawa Shoten, 1991), and the like.

In the present invention, the phrase "(those) bind to HLA-A24 antigen, thereby allowing to be recognized by CTL" means that the tumor antigen peptide of the present invention binds to HLA-A24 antigen, to thereby form a complex, whereby the resulting complex can be recognized by CTL.

Whether or not the tumor antigen peptide of the present invention binds to HLA-A24 antigen, thereby allowing to be recognized by CTL, namely whether or not the peptide possesses an activity as an HLA-A24-restricted tumor antigen peptide, can be evaluated by an assay described, for instance, in *J. Immunol.*, 154, 2257, 1995. Concretely, when peripheral blood lymphocytes are isolated from HLA-A24 antigen-positive human and candidate peptides are added thereto to stimulate in vitro, it can be evaluated by determining whether or not CTLs that specifically recognize the candidate peptide-pulsed HLA-A24-positive cells are induced. Here, the presence or absence of the induction of the CTLs can be examined, for instance, by assaying an amount of various cytokines (for instance, IFN-γ) produced by CTLs in reaction with the antigen peptide presenting cells by means of enzyme-linked immunosorbent assay (ELISA) or the like. As the antigen peptide presenting cells (target cells) during the assay, there are included, for instance, esophageal cancer cell line KE-4 (FERM BP-5955). In addition, the induction can be examined by the method for assaying CTL toxicity on $^{51}$Cr-labeled antigen peptide presenting cells ($^{51}$Cr-release assay, *Int. J. Cancer*, 58:317, 1994). Further, the induction can be examined by pulsing with candidate peptides to cells resulting from introduction of an expression plasmid into, for instance, COS-7 cells (ATCC No. CRL1651) and VA-13 cells (RIKEN CELL BANK), the expression plasmid for expressing HLA-A24 cDNA [*Cancer Res.*, 55:4248–4252 (1995); Genbank Accession No. M64740]; reacting KE-4CTL (FERM BP-5954), or CTLs prepared in the manner described above, or the like with the resulting cells; and assaying an amount of various cytokines (for instance, IFN-γ) that are produced by CTLs.

The assay described herein may be also referred to as "assay for the tumor antigen peptide" hereinbelow.

In the present invention, the phrase "derivative possessing functionally equivalent characteristics to the tumor antigen peptide" (which may simply be referred to hereinbelow as a tumor antigen peptide derivative, in some cases) refers to a modified product resulting from modification of one or several amino acid residues of the amino acid sequence of the tumor antigen peptide of the present invention, the modified product possessing characteristics as the tumor antigen peptide that binds to HLA-A24 antigen, thereby allowing to be recognized by CTL. In other words, the tumor antigen peptide derivative of the present invention encompasses all modified products each resulting from modification of one or several amino acid residues in the amino acid sequence of the tumor antigen peptide of the present invention, the modified product possessing an activity as the tumor antigen peptide that binds to HLA-A24 antigen, thereby allowing to be recognized by CTL.

Here, the term "modification" of the amino acid residues means substitution, deletion and/or addition of amino acid residues (including addition of an amino acid to N-terminal or C-terminal of the peptide), and there is preferably included the substitution of amino acid residues. In the case of the modification as the substitution of amino acid residues, the number and positions of the amino acid residues to be substituted can be arbitrary as long as the activity as the tumor antigen peptide is maintained.

Incidentally, there are regularities (motifs) in the sequence of the antigen peptide, wherein the antigen peptide binds to an HLA antigen, thereby being presented. In the case of HLA-A24 antigen, there have been known that 2nd amino acid in N-terminal among the peptides having 8 to 11 amino acids is phenylalanine, tyrosine, methionine or tryptophan, and that the amino acid at C-terminal is phenylalanine, leucine, isoleucine, tryptophan or methionine (*Immunogenetics*, 41:178, 1995; *J. Immunol.*, 152:3913, 1994; *J. Immunol.*, 155:4307, 1994). In addition, the amino acid residues possessing resembling characteristics to amino acids which can be chosen from the viewpoint of the motifs can be accepted. Therefore, the tumor antigen peptide derivatives of the present invention encompass those derivatives resulting from substitution of an amino acid at a position in which an amino acid can be substituted from the viewpoint of the motifs, namely an amino acid at position 2 and/or at C-terminal, by another amino acid, the derivatives possessing an activity as a tumor antigen peptide. There are preferably included tumor antigen peptide derivatives resulting from substitution of an amino acid at position 2 and/or at C-terminal by an amino acid that can be substituted from the viewpoint of the above-mentioned motifs, the derivatives possessing an activity as a tumor antigen peptide. It is preferable that the length of the peptide is 8 to 11 amino acids or so, from the viewpoint of presentation of the antigen peptide by binding to HLA-A24.

Concrete examples thereof include all or a part of an amino acid sequence resulting from substitution of an amino acid at position 2 of the amino acid sequence of any one of SEQ ID NO: 1 to SEQ ID NO: 5 by phenylalanine, tyrosine, methionine or tryptophan, and/or substitution of an amino acid at C-terminal of the amino acid sequence of any one of SEQ ID NO: 1 to SEQ ID NO: 5 by phenylalanine, leucine, isoleucine, tryptophan or methionine. Examples of these modified peptides are shown in SEQ ID NO: 6 to SEQ ID NO: 10, respectively. In addition, the tumor antigen peptide derivatives of the present invention encompass a peptide comprising all or a part of the amino acid sequence of SEQ ID NO: 17.

Here, the tumor antigen peptide of the present invention is a peptide having a part of SART-1, and comprising all or a part of the amino acid sequence having HLA-A24 binding motif as mentioned above. Similarly, as a peptide having a part of SART-1 and having HLA-A24 binding motif, there are included peptides consisting of the amino acid sequences of SEQ ID NO: 11 to SEQ ID NO: 16. There also exist those possessing an activity of a tumor antigen peptide, a peptide comprising all or a part of the amino acid sequence of these SEQ ID NO: 11 to SEQ ID NO: 16, or a peptide derivative resulting from the modification of the peptide on the basis of the motifs mentioned above, which can be easily chosen by the above assay for the activity.

Whether or not the tumor antigen peptide derivative of the present invention possesses functionally equivalent characteristics to the tumor antigen peptide can be identified by synthesizing, in the same manner as the tumor antigen peptide of the present invention, the peptide to be a candidate on the basis of the peptide synthesis method mentioned above, and subjecting the resulting peptide to the assay for the tumor antigen peptide mentioned above.

The tumor antigen peptide or the derivative thereof of the present invention can be used as a therapeutic agent or prophylactic agent for a tumor by combining at least one member or two or more members of the tumor antigen peptide or the derivative thereof. The present invention provides a therapeutic agent or prophylactic agent for a tumor, comprising the tumor antigen peptide or the derivative thereof as an active ingredient. When the therapeutic agent or prophylactic agent for a tumor of the present invention is administered to an HLA-A24-positive and SART-1-positive patient, the tumor antigen peptide or the derivative thereof is presented to the HLA-A24 antigen of the antigen presenting cells, so that the presented HLA-A24 antigen complex-specific CTLs are proliferated, whereby the tumor cells can be destroyed. Therefore, the treatment or prophylaxis for a tumor can be accomplished. Since SART-1 is expressed in a wide range in squamous cell carcinomas such as esophageal cancer and lung cancer, it is advantageous that the therapeutic agent or prophylactic agent of the present invention has a wide application range. Further, while the squamous cell carcinomas mentioned above show resistivity to chemotherapy or radiotherapy in many cases, the therapeutic effects can be enhanced by the combined use of the therapeutic agent for a tumor of the present invention.

The therapeutic agent or prophylactic agent for a tumor of the present invention can be administered together with an adjuvant, or administered in a preparation in the form of particles in order to effectively establish the cellular immunity. As the adjuvants, those described in the publication (*Clin. Microbiol. Rev.*, 7:277–289, 1994) and the like can be applied. In addition, there can be also considered liposome preparations, preparations in the form of particles conjugated to beads having a diameter of several micrometers, preparations conjugated to lipids, and the like. As the method for administration, there can be considered intracutaneous injection, subcutaneous injection, intravenous injection, and the like. The dose of the tumor antigen peptide or the derivative thereof of the present invention in the preparation can be properly adjusted depending upon the disease to be treated, the age and body weight of a patient, and the like. It is preferable that each dose of usually 0.0001 to 1000 mg, preferably 0.001 to 1000 mg, more preferably 0.1 to 10 mg is administered once every several days to every several months.

Further, as the therapeutic agent or prophylactic agent for a tumor of the present invention, besides the case where the tumor antigen peptide or the derivative thereof of the present invention is contained as an active ingredient as mentioned above, DNA encoding the tumor antigen peptide or the derivative thereof of the present invention, or a polypeptide, which is an expression product of the DNA, can be also contained as an active ingredient for the therapeutic agent or prophylactic agent for a tumor of the present invention as described below.

In other words, recently, there have been employed some techniques utilizing DNAs encoding a so-called "polytope," wherein plural CTL epitopes are conjugated, for DNA vaccines (see, for instance, *Journal of Immunology*, 160, 1717, 1998 or the like). Therefore, a recombinant DNA prepared by ligating at least one member, or two or more members of DNA encoding the tumor antigen peptide or the derivative thereof of the present invention, and in some cases further ligating DNA encoding another tumor antigen peptide, is incorporated into an appropriate expression vector, whereby the resulting product can be used as an active ingredient for a therapeutic agent or prophylactic agent for a tumor. In addition, not only the recombinant DNA mentioned above can be used as a therapeutic agent or prophylactic agent for a tumor but also a polypeptide resulting from expression of the recombinant DNA in host cells can be used as an active ingredient of a therapeutic agent or prophylactic agent for a tumor.

Here, the term "recombinant DNA" can be easily prepared on the bases of DNA synthesis and ordinary genetic engineering techniques in accordance with the basic textbooks such as *Molecular Cloning 2nd Edt.*, Cold Spring Harbor Laboratory Press (1989). In addition, the incorporation of this recombinant DNA into an expression vector can be carried out in accordance with the basic textbook mentioned above or the like.

Whether or not the prepared recombinant DNA of the present invention produces a tumor antigen peptide which binds to HLA-A24 antigen, thereby allowing to be recognized by CTL can be determined by, for instance, the following method.

Concretely, first the cells such as COS-7 cells (ATCC CRL1651) and VA-13 cells (RIKEN CELL BANK) were double-transfected with an expression plasmid carrying the recombinant DNA to be candidates, and with an expression plasmid carrying cDNA encoding HLA-A24 antigen [*Cancer Res.*, 55:4248–4252 (1995); Genbank Accession No. M64740]. The transfection can be carried out by lipofectin method or the like using, for instance, a lipofectamine reagent (manufactured by GIBCO BRL). Thereafter, whether or not the candidate DNAs possess an activity can be evaluated by adding to act HLA-A24-restricted CTLs (for instance, KE-4CTL, FERM BP-5954), and determining the amount of various cytokines (for instance, IFN-γ) produced by the reaction of the CTLs by means of, for instance, ELISA method or the like.

When the recombinant DNA of the present invention is applied for the therapeutic agent or prophylactic agent for a tumor, the following method can be employed.

Concretely, as the method for introducing the recombinant DNA of the present invention into cells, any of the methods such as a method using a viral vector, and other methods [*Nikkei Science*, April, 1994, 20–45; *Gekkan Yakuji* (*Monthly Medicine*), 36(1), 23–48 (1994); *Jikken Igaku Zokan* (*Experimental Medicine, Extra Issue*), 12(15) (1994), and references cited therein, and the like] can be applied.

As the method using a viral vector, there are included, for instance, a method of incorporating the DNA of the present invention into DNA virus or RNA virus such as retrovirus, adenovirus, adeno-associated virus, herpes virus, vaccinia virus, poxvirus, poliovirus and Sindbis virus. Among these methods, the method using retrovirus, adenovirus, adeno-associated virus, vaccinia virus, or the like is especially preferred.

As other methods, there are included a method of directly administering an expression plasmid intramuscularly (DNA vaccination method), liposome method, lipofectin method, microinjection method, calcium phosphate method, electroporation method, and the like, and the DNA vaccination method and the liposome method are especially preferable.

In order to actually make the recombinant DNA of the present invention act as a pharmaceutical, there are employed in vivo method comprising directly introducing DNA into the body; and ex vivo method comprising collecting a certain kind of cells from a human, introducing DNA into the collected cells extracorporeally, and reintroducing the gene-incorporated cells into the body [*Nikkei Science*, April, 1994, 20–45; *Gekkan Yakuji*, 36(1), 23–48 (1994); *Jikken Igaku Zokan*, 12(15), 1994; and references cited therein, and the like]. In vivo method is more preferred.

When administered by in vivo method, the pharmaceutical can be administered via an appropriate dosage route depending on the diseases and symptoms to be treated, and other factors. For example, it may be administered intravenously, intraarterially, subcutaneously, intracutaneously, intramuscularly, or the like. When administered by in vivo method, the pharmaceuticals may take such a preparation form for liquid preparations. Generally, the pharmaceutical is prepared as an injection, comprising the recombinant DNA of the present invention or the like as an active ingredient, to which a conventional carrier may be added as occasion demands. In liposomes or membrane-fused liposomes (such as Sendai virus (HVJ)-liposomes) each comprising the recombinant DNA of the present invention, there can be prepared into liposome preparations in the form of suspension, cryogen, centrifugally-concentrated cryogen or the like.

The content of the recombinant DNA of the present invention in the preparation can be properly adjusted depending upon, for example, the disease to be treated, the age and body weight of a patient, and the like. It is preferable that 0.0001 to 100 mg, preferably 0.001 to 10 mg, of the recombinant DNA of the present invention is usually administered once every several days to every several months.

By the administration of the recombinant DNA of the present invention as described above to a patient with a tumor, a polypeptide corresponding to the recombinant DNA in the antigen presenting cells is highly expressed. Thereafter, the individual tumor antigen peptides produced by intracellular degradation bind to an HLA antigen, to form complexes, so that the complexes are presented on the surface of the antigen presenting cells in high densities, whereby the complex-specific CTLs are efficiently proliferated in the body, and caused to further destroy the tumor cells. As described above, the prophylaxis or treatment for a tumor is achieved.

In addition, the "polypeptide" obtainable by expressing the recombinant DNA mentioned above can be expressed and produced by introducing an expression plasmid into a host cell, to give a transformant, the expression plasmid being prepared by incorporating the recombinant DNA mentioned above into an appropriate expression vector (for instance, pSV-SPORT1 or the like), and culturing the resulting transformant in an appropriate medium. Here, the host cell include cells of prokaryotes such as *Escherichia coli*; unicellular eukaryotes such as yeasts; and multicellular eukaryotes such as insects and animals. In addition, as a method for introducing the gene into the host cell, there are included calcium phosphate method, DEAE-dextran method, electric pulse method, and the like. The polypeptide obtained in the manner described above can be isolated and purified by general biochemical procedures. In addition, whether or not the resulting polypeptide produces a tumor antigen peptide which binds to HLA-A24, thereby allowing to be recognized by CTL can be evaluated, for instance, by incorporating the polypeptide of the present invention into phagocytes such as macrophage to produce peptide fragments intracellularly, thereafter adding CTLs such as KE-4CTL to a complex formed between the resulting peptide fragments and the HLA-A24 antigen, to act thereon, and assaying the amount of various cytokines (for instance, IFN-γ) produced in reaction with the CTLs.

When the polypeptide of the present invention is applied as a therapeutic agent or prophylactic agent for a tumor, the polypeptide can be administered with the same dosage form, methods of administration, and dose as the tumor antigen peptide or the derivative thereof of the present invention mentioned above. When the polypeptide of the present invention is administered to a patient with a tumor, the polypeptide is incorporated into the antigen presenting cell, and thereafter individual tumor antigen peptides which are produced by intracellular degradation bind with the HLA antigen, to form complexes, so that the complexes are presented in high densities on the surface of the antigen presenting cells, whereby the CTLs specific to the complexes are efficiently proliferated in the body and further cause to destroy tumor cells. As described above, the prophylaxis or treatment for a tumor is achieved.

The present invention provides an antibody which specifically binds to the tumor antigen peptide or the derivative thereof of the present invention. The antibody is easily prepared in accordance with the method described in, for instance, *Antibodies: A Laboratory Manual*, edited by Lane, H. D. et al., published by Cold Spring Harbor Laboratory Press, New York, 1989, or the like. Concretely, an antibody capable of recognizing the tumor antigen peptide or the derivative thereof, and further an antibody capable of neutralizing its activity can be easily prepared by properly immunizing an animal by using the tumor antigen peptide or the derivative thereof of the present invention by a conventional method. The application of the antibody includes affinity chromatography, immunological diagnosis, and the like. The immunological diagnosis can be appropriately selected from immunoblotting method, radioimmunoassay (RIA), enzyme-linked immunosorbent assay (ELISA), fluorescence or luminescence assay, and the like.

The tumor antigen peptide or the derivative thereof of the present invention, or the recombinant DNA of the present invention or a polypeptide obtainable by expressing the recombinant DNA can be utilized in vitro in the treatment of a patient with a tumor as follows.

Concretely, the present invention provides antigen presenting cell which presents a complex formed between the HLA-A24 antigen and the tumor antigen peptide or the derivative thereof of the present invention on the surface of the isolated cells from a patient with tumor, the cells possessing an ability for antigen presentation. Here, the phrase "cells possessing an ability for antigen presentation" is not particularly limited, as long as they are cells which express the HLA-A24 antigen capable of presenting the tumor antigen peptide or the derivative thereof of the present invention on the cell surface. The dentritic cells which are known to possess a high ability for antigen presentation are especially preferable.

In addition, as substances to be added in order to prepare the antigen presenting cell of the present invention from the cells possessing an ability for antigen presentation mentioned above, there may be used not only the tumor antigen peptide or the derivative thereof of the present invention but also the recombinant DNA or polypeptide of the present invention.

The antigen presenting cell of the present invention is obtained by isolating cells possessing an ability for antigen presentation from a patient with a tumor, and pulsing extracorporeally the tumor antigen peptide or the derivative thereof of the present invention, or the polypeptide of the present invention, to prepare a complex formed between the HLA-A24 antigen and the peptide mentioned above or the derivative thereof (*Cancer Immunol. Immunother.*, 46:82, 1998; *J. Immunol.*, 158:1796, 1997; *Cancer Res.*, 59:1184, 1999). When the dentritic cells are used, the antigen presenting cells of the present invention can be prepared by, for instance, isolating lymphocytes from peripheral blood of a patient with a tumor by means of Ficol method, thereafter eliminating non-adherent cells, culturing adherent cells in the presence of GM-CSF and IL-4, to induce the dentritic cells, and culturing the dentritic cells together with the tumor antigen peptide or the polypeptide of the present invention, thereby pulsing the dentritic cells therein.

In addition, when the antigen presenting cell of the present invention is prepared by introducing the recombinant DNA of the present invention into cells possessing an ability for antigen presentation mentioned above, the preparation can be carried out by referring to *Cancer Res.*, 56:5672, 1996, *J. Immunol.*, 161:5607, 1998, or the like. In addition, the antigen presenting cell can be similarly prepared in the form of RNA as well as that in the form of DNA. In this case, the preparation can be carried out by referring to *J. Exp. Med.*, 184:465, 1996, or the like.

The present invention provides a therapeutic agent for a tumor, comprising the antigen presenting cell mentioned above as an active ingredient. It is preferable that the therapeutic agent contains physiological saline, phosphate buffered saline (PBS), a medium, and the like, in order to stably maintain the antigen presenting cells. As the method of administration, there are included intravenous administration, subcutaneous administration, and intracutaneous administration.

By reintroducing the therapeutic agent mentioned above into the body of the patient, the specific CTLs are efficiently induced in the body of a patient who is HLA-A24 positive and SART-1 positive, whereby the tumor can be treated.

Further, as in vitro utilization of the tumor antigen peptide or the derivative thereof of the present invention and the like, there is included utilization in the following adoptive immunotherapy.

Concretely, in melanomas, a therapeutic effect has been found in the adoptive immunotherapy wherein tumor-infiltrating T cell of the patient himself is extracorporeally cultured in a large amount, and the culture is reintroduced to the patient (*J. Natl. Cancer. Inst.*, 86:1159, 1994). In addition, in murine melanomas, metastatic suppression has been found by stimulating splenocytes with tumor antigen peptide TRP-2 in vitro to proliferate CTLs specific to the tumor antigen peptide, and administering the CTLs to melanoma-transplanted mouse (*J. Exp. Med.*, 185:453, 1997). This finding is based on the results of proliferating CTLs that specifically recognize a complex formed between the HLA antigen of the antigen presenting cells and the tumor antigen peptide in vitro. Therefore, it is considered that this therapeutic method in which tumor-specific CTLs are proliferated by stimulating peripheral blood lymphocytes of a patient in vitro using the tumor antigen peptide or the derivative thereof of the present invention, or the recombinant DNA or polypeptide of the present invention, and thereafter reintroducing these CTLs to the patient, is useful.

The present invention also provides CTL that specifically recognizes a complex formed between the HLA-A24 antigen mentioned above, and the tumor antigen peptide or the derivative thereof of the present invention.

Further, the present invention also provides a therapeutic agent for a tumor, comprising the CTL of the present invention as an active ingredient. It is preferable that the therapeutic agent contains physiological saline, phosphate buffered saline (PBS), a medium, and the like, in order to stably maintain the CTLs. As the method of administration, there are included intravenous administration, subcutaneous administration, and intracutaneous administration.

By reintroducing the therapeutic agent mentioned above into the body of the patient, the cytotoxic actions on the tumor cells by the CTLs in the body of a HLA-24-positive and SART-1-positive patient are enhanced, so that the tumor cells are destroyed, whereby the tumor can be treated.

In addition, the tumor antigen peptide and the derivative thereof of the present invention can be used as an ingredient for a diagnostic agent for diagnosing a tumor. Concretely, the presence of an antibody in a sample (for instance, blood, tumor tissues, and the like) obtained from a patient who is suspected to have a tumor is detected by using the tumor antigen peptide or the derivative thereof of the present invention per se as a diagnostic agent, whereby early detection, recurrence, or metastasis for a tumor can be diagnosed. Also, the diagnostic agent can be utilized in the selection of a patient with a tumor, the patient to whom a pharmaceutical comprising the tumor antigen peptide and the like of the present invention can be applied as an active ingredient. Concretely, the diagnosis can be made by using immunoblotting method, RIA, ELISA, fluorescence or luminescence assay, or the like.

In addition, recently, there has been established a new detection method for detecting antigen-specific CTLs by using a complex formed between an antigen peptide and an HLA antigen (*Science*, 274:94, 1996). The tumor antigen-specific CTLs are detected by subjecting a complex to the detection method mentioned above, the complex being formed between the tumor antigen peptide or the derivative thereof of the present invention and the HLA antigen, whereby early detection, recurrence, or metastasis for a tumor can be diagnosed. Also, the detection method can be utilized in the selection of a patient with a tumor, the patient to whom a pharmaceutical comprising the tumor antigen peptide and the like of the present invention can be applied as an active ingredient, the evaluation of the therapeutic effects by the pharmaceutical, and the like. In other words, in the present invention, there is also provided a diagnostic agent for a tumor, comprising the tumor antigen peptide or the derivative thereof of the present invention.

Concretely, the above-mentioned diagnosis can be made by preparing a tetramer of a complex formed between an HLA antigen and the tumor antigen peptide, the HLA antigen being fluorescent labeled in accordance with the method described in the publication (*Science*, 274:94, 1996), and quantifying the antigen peptide-specific CTLs in the peripheral blood lymphocytes of a patient suspected to have a tumor with a flow cytometer using the resulting tetramer.

The present invention will be concretely explained by the examples, without by no means intending to limit the scope of the present invention to these examples.

REFERENCE EXAMPLE 1

Establishment of Cytotoxic T Cell Line (CTL) Against Esophageal Cancer Cell Line In accordance with the description in Nakao et al., *Cancer Res.*, 55:4248–4252, 1995, CTL line against an esophageal cancer cell line KE-4 of which tissue type is classified as squamous cell carcinomas were established from peripheral blood monocytes of a patient, and named KE-4CTL to be used in experiments. The esophageal cancer cell line KE-4 and KE-4CTL have been deposited under the accession numbers of FERM BP-5955 and FERM BP-5954, respectively, with the National Institute of Bioscience and Human-Technology, Agency of Industrial Science and Technology, of which the address is 1–3, Higashi 1-chome, Tsukuba-shi, Ibaraki-ken, since May 23, 1997. In addition, in accordance with the above-mentioned report of Nakao et al., typing of HLA-A locus of KE-4 was carried out, and it was confirmed that these cell lines are HLA-A2402 and HLA-A2601.

EXAMPLE 1

Selection and Synthesis of Tumor Antigen Peptide

There have been known that the sequence of the antigen peptide has regularities (motifs), wherein the antigen peptide binds to HLA molecule to thereby be presented, and in the case of HLA-A24, motif is tyrosine, phenylalanine, methionine or tryptophan at 2nd amino acid in N-terminal, and phenylalanine, tryptophan, leucine, isoleucine or methionine at the C-terminal end (*Immunogenetics*, 41:178, 1995; *J. Immunol.*, 152:3913, 1994; *J. Immunol.*, 155:4307, 1994). From the amino acid sequence of the tumor antigen protein SART-1 which the present inventors identified (the amino acid sequence of SEQ ID NO: 1 in WO 97/46676), peptide portions having 8 to 11 amino acids having the above-mentioned motifs were selected. Among the peptide portions, a peptide having positions 619th to 627th on the amino acid sequence of SART-1 was named "619–627" (SEQ ID NO: 11); a peptide having positions 619th to 628th, "619–628" (SEQ ID NO: 12); a peptide having positions 672nd to 681st, "672–681" (SEQ ID NO: 13); a peptide having positions 684th to 694th, "684–694" (SEQ ID NO: 14); a peptide having positions 703rd to 710th, "703–710" (SEQ ID NO: 15); a peptide having positions 711th to 720th, "711–720" (SEQ ID NO: 16); a peptide having positions 725th to 733rd, "725–733" (SEQ ID NO: 1); a peptide having positions 740th to 750th, "740–750" (SEQ ID NO: 2); a peptide having positions 746th to 755th, "746–755" (SEQ ID NO: 3); a peptide having positions 746th to 756th, "746–756" (SEQ ID NO: 4); and a peptide having positions 758th to 766th, "758–766" (SEQ ID NO: 5), respectively. Among these peptides, the peptides of SEQ ID NO: 1 to SEQ ID NO: 4, and the peptide named "758–766*" of SEQ ID NO: 17 corresponding to a modified product of the peptide of SEQ ID NO: 5 were each synthesized by the solid phase method described below.

[1] Synthesis of SART-1 "725–733" Ala-Phe-Arg-Gln-Leu-Ser-His-Ar-Phe (SEQ ID NO: 1)

As the resin, there was used Fmoc-Phe-Alko Resin (0.56 mmol/g, 100 to 200 mesh). The synthesis was initiated in accordance with Schedule 1 detailed below using 100 mg of this resin, to thereby sequentially couple Fmoc-Arg(Pmc)-OH, Fmoc-His(Trt)-OH, Fmoc-Ser(tBu)-OH, Fmoc-Leu-OH, Fmoc-Gln-OH, Fmoc-Arg(Pmc)-OH, Fmoc-Phe-OH, and Fmoc-Ala-OH. After coupling, the procedures up to Step 3 of Schedule 1 were carried out. As a result, a peptide resin was obtained.

Two milliliters of Reagent K (5% phenol, 5% thioanisole, 5% $H_2O$, 2.5% ethanedithiol/TFA solution) was added to the resulting peptide resin, and the mixture was reacted at room temperature for 2.5 hours. Ten milliliters of diethyl ether was added to the reaction mixture under ice-cooling, and the mixture was stirred for 10 minutes. The resulting mixture was filtered, and washed with 10 ml of diethyl ether. Ten milliliters of an aqueous acetic acid was added to the residue, and stirred for 30 minutes. Thereafter, the resin was separated by filtration, and washed with 4 ml of an aqueous acetic acid. The filtrate was lyophilized, and thereafter the resulting crude peptide was dissolved in an aqueous acetic acid. The solution was injected to a reverse phase-system filler COSMOSIL 5C18-AR column (28φ×250 mm), which was previously equilibrated with 0.1% aqueous TFA. The column was then washed with 0.1% aqueous TFA. Thereafter, the acetonitrile concentration was increased up to 20% in 200 minutes, and elution was carried out at a flow rate of 7 ml/min. The eluent was monitored at an absorbance of 220 nm to collect a fraction containing a desired product. The collected fraction was lyophilized, to give 18.4 mg of Ala-Phe-Arg-Gln-Leu-Ser-His-Arg-Phe (SEQ ID NO: 1).

The resulting peptide exhibited a retention time of 18.3 minutes in the analysis by a 0 to 60% linear concentration gradient elution method of acetonitrile containing 0.1% TFA using a reverse phase-system filler YMC-PACK ODS-AM column (4.6φ×250 mm). The amino acid analysis value and the mass spectroscopic value were consistent with those of the theoretical values.

Amino Acid Analysis

Hydrolysis: 1% phenol/6 N aqueous hydrochloric acid, 110° C., 24 hours

Analysis method: ninhydrin method

| | | |
|---|---|---|
| Ser: 0.82 | (1) | |
| Glx: 0.96 | (1) | |
| Ala: 0.99 | (1) | |
| *Leu: 1.00 | (1) | |
| Phe: 1.91 | (2) | |
| His: 0.92 | (1) | |
| Arg: 1.72 | (2) | |

*standard amino acid
Inside parenthesis ( ) being theoretical values.
Mass spectrometry (FAB) [M + H]⁺: 1161

Schedule 1

| Steps | Period of Time (minutes) × number of repetitions |
|---|---|
| 1. (Washing) DMF 1.2 ml | 1 × 2 |
| 2. (Deprotecting) 50% piperidine/DMF | 12 × 1 |
| 3. (Washing) DMF 1.2 ml | 1 × 7 |

-continued

| Steps | Period of Time (minutes) × number of repetitions |
|---|---|
| 4. (Coupling) Each amino group-protecting amino acid (5 equivalents)/ NMP solution 0.9 ml, DIC (5 equivalents)/ NMP solution 0.3 ml | 30 × 1 |
| 5. (Washing) DMF 1.2 ml | 1 × 2 |
| 6. (Coupling) Each amino group-protecting amino acid (5 equivalents)/ NMP solution 0.9 ml, DIC (5 equivalents)/ NMP solution 0.3 ml | 30 × 1 |
| 7. (Washing) DMF 1.2 ml | 1 × 4 |

[2] Synthesis of SART-1 "740–750" Lys-Met-Lys-Thr-Glu-Arg-Arg-Met-Lys-Lys-Leu (SEQ ID NO: 2)

As the resin, there was used Fmoc-Leu-Alko Resin (0.57 mmol/g, 100 to 200 mesh). In the same manner as in item [1] above, coupling of Fmoc-Lys(Boc)-OH, Fmoc-Lys(Boc)-OH, Fmoc Met-OH, Fmoc-Arg(Pmc)-OH, Fmoc-Arg(Pmc)-OH, Fmoc-Glu(OtBu)-OH, Fmoc-Thr(tBu)-OH, Fmoc-Lys (Boc)-OH, Fmoc-Met-OH and Fmoc-Lys(Boc)-OH was sequentially carried out using 100 mg of this resin, and thereafter deprotection was carried out. The resulting crude peptide was dissolved in an aqueous acetic acid. The solution was injected to a reverse phase-system filler COSMOSIL 5C18-AR column (28φ×250 mm), which was previously equilibrated with 0.1% aqueous TFA. The column was then washed with 0.1% aqueous TFA. Thereafter, the acetonitrile concentration was increased up to 21% in 200 minutes, and elution was carried out at a flow rate of 7 ml/min. The eluent was monitored at an absorbance of 220 nm to collect a fraction containing a desired product. The collected fraction was lyophilized, to give 38.1 mg of Lys-Met-Lys-Thr-Glu-Arg-Arg-Met-Lys-Lys-Leu (SEQ ID NO: 2).

The resulting peptide exhibited a retention time of 15.3 minutes in the analysis by a 0 to 60% linear concentration gradient elution method of acetonitrile containing 0.1% TFA using a reverse phase-system filler YMC-PACK ODS-AM column (4.6φ×250 mm). The amino acid analysis value (except that Met was undetectable) and the mass spectroscopic value were consistent with those of the theoretical values.

Amino Acid Analysis

Hydrolysis: 1% phenol/6 N aqueous hydrochloric acid, 110° C., 24 hours Analysis method: ninhydrin method Inside parenthesis ( ) being theoretical values.

| | |
|---|---|
| Thr: 0.88 | (1) |
| Glx: 0.91 | (1) |
| *Leu: 1.00 | (1) |
| Lys: 3.39 | (4) |
| Arg: 1.64 | (2) |

*standard amino acid
Mass spectrometry (FAB) [M + H]⁺: 1448

[3] Synthesis of SART-1 "746–755" Arg-Met-Lys-Lys-Leu-Asp-Glu-Glu-Ala-Leu (SEQ ID NO: 3)

As the resin, there was used Fmoc-Leu-Alko Resin (0.57 mmol/g, 100 to 200 mesh). In the same manner as in item [1] above, coupling of Fmoc-Ala-OH, Fmoc-Glu(OtBu)-OH, Fmoc-Glu(OtBu)-OH, Fmoc-Asp(OtBu)-OH, Fmoc-Leu-OH, Fmoc-Lys(Boc)-OH, Fmoc-Lys(Boc)-OH, Fmoc-Met-OH and Fmoc-Arg(Pmc)-OH was sequentially carried out using 100 mg of this resin, and thereafter deprotection was carried out. The resulting crude peptide was dissolved in an aqueous acetic acid. The solution was injected to a reverse phase-system filler COSMOSIL 5C18-AR column (28φ× 250 mm), which was previously equilibrated with 0.1% aqueous TFA. The column was then washed with 0.1% aqueous TFA. Thereafter, the acetonitrile concentration was increased up to 20% in 200 minutes, and elution was carried out at a flow rate of 7 ml/min. The eluent was monitored at an absorbance of 220 nm to collect a fraction containing a desired product. The collected fraction was lyophilized, to give 24.6 mg of Arg-Met-Lys-Lys-Leu-Asp-Glu-Glu-Ala-Leu (SEQ ID NO: 3).

The resulting peptide exhibited a retention time of 17.4 minutes in the analysis by a 0 to 60% linear concentration gradient elution method of acetonitrile containing 0.1% TFA using a reverse phase-system filler YMC-PACK ODS-AM column (4.6φ×250 mm). The amino acid analysis value (except that Met was undetectable) and the mass spectroscopic value were consistent with those of the theoretical values.

Amino Acid Analysis

Hydrolysis: 1% phenol/6 N aqueous hydrochloric acid, 110° C., 24 hours Analysis method: ninhydrin method

| Inside parenthesis ( ) being theoretical values. | |
|---|---|
| Asx: 0.95 | (1) |
| Glx: 1.85 | (2) |
| Ala: 0.97 | (1) |
| *Leu: 2.00 | (2) |
| Lys: 1.72 | (2) |
| Arg: 0.81 | (1) |

*standard amino acid
Mass spectrometry (FAB) [M + H]$^+$: 1232

[4] Synthesis of SART-1 "746–756"

Arg-Met-Lys-Lys-Leu-Asp-Glu-Glu-Ala-Leu-Leu (SEQ ID NO: 4)

As the resin, there was used Fmoc-Leu-Alko Resin (0.57 mmol/g, 100 to 200 mesh). In the same manner as in item [1] above, coupling of Fmoc-Leu-OH, Fmoc-Ala-OH, Fmoc-Glu(OtBu)-OH, Fmoc-Glu(OtBu)-OH, Fmoc-Asp(OtBu)-OH, Fmoc-Leu-OH, Fmoc-Lys(Boc)-OH, Fmoc-Lys(Boc)-OH, Fmoc-Met-OH and Fmoc-Arg(Pmc)-OH was sequentially carried out using 100 mg of this resin, and thereafter deprotection was carried out. The resulting crude peptide was dissolved in an aqueous acetic acid. The solution was injected to a reverse phase-system filler COSMOSIL 5C18-AR column (28φ×250 mm), which was previously equilibrated with 0.1% aqueous TFA. The column was then washed with 0.1% aqueous TFA. Thereafter, the acetonitrile concentration was increased up to 23% in 200 minutes, and elution was carried out at a flow rate of 7 ml/min. The eluent was monitored at an absorbance of 220 nm to collect a fraction containing a desired product. The collected fraction was lyophilized, to give 28.8 mg of Arg-Met-Lys-Lys-Leu-Asp-Glu-Glu-Ala-Leu-Leu (SEQ ID NO: 4).

The resulting peptide exhibited a retention time of 19.6 minutes in the analysis by a 0 to 60% linear concentration gradient elution method of acetonitrile containing 0.1% TFA using a reverse phase-system filler YMC-PACK ODS-AM column (4.6φ×250 mm). The amino acid analysis value (except that Met was undetectable) and the mass spectroscopic value were consistent with those of the theoretical values.

Amino Acid Analysis

Hydrolysis: 1% phenol/6 N aqueous hydrochloric acid, 110° C., 24 hours

Analysis method: ninhydrin method

| Inside parenthesis ( ) being theoretical values. | |
|---|---|
| Asx: 0.98 | (1) |
| Glx: 1.87 | (2) |
| Ala: 0.97 | (1) |
| *Leu: 3.00 | (3) |
| Lys: 1.70 | (2) |
| Arg: 0.83 | (1) |

*standard amino acid
Mass spectrometry (FAB) [M + H]$^+$: 1345

[5] Synthesis of SART-1 "758–766*"

Lys-Met-Ser-Ser-Ser-Asp-Pro-Thr-Leu (SEQ ID NO: 17)

As the resin, there was used Fmoc-Leu-Alko Resin (0.57 mmol/g, 100 to 200 mesh). In the same manner as in item [1] above, coupling of Fmoc-Thr(tBu)-OH, Fmoc-Pro-OH, Fmoc-Asp(OtBu)-OH, Fmoc-Ser(tBu)-OH, Fmoc-Ser(tBu)-OH, Fmoc-Ser(tBu)-OH, Fmoc-Met-OH and Fmoc-Lys(Boc)-OH was sequentially carried out using 100 mg of this resin, and thereafter deprotection was carried out. The resulting crude peptide was dissolved in an aqueous acetic acid. The solution was injected to a reverse phase-system filler COSMOSIL 5C18-AR column (28φ×250 mm), which was previously equilibrated with 0.1% aqueous TFA. The column was then washed with 0.1% aqueous TFA. Thereafter, the acetonitrile concentration was increased up to 17% in 200 minutes, and elution was carried out at a flow rate of 7 ml/min. The eluent was monitored at an absorbance of 220 nm to collect a fraction containing a desired product. The collected fraction was lyophilized, to give 24.1 mg of Lys-Met-Ser-Ser-Ser-Asp-Pro-Thr-Leu (SEQ ID NO: 17).

The resulting peptide exhibited a retention time of 16.3 minutes in the analysis by a 0 to 60% linear concentration gradient elution method of acetonitrile containing 0.1% TFA using a reverse phase-system filler YMC-PACK ODS-AM column (4.6φ×250 mm). The amino acid analysis value (except that Met was undetectable) and the mass spectroscopic value were consistent with those of the theoretical values.

Amino Acid Analysis

Hydrolysis: 1% phenol/6 N aqueous hydrochloric acid, 110° C., 24 hours

Analysis method: ninhydrin method

| Inside parenthesis ( ) being theoretical values. | |
|---|---|
| Asx: 0.90 | (1) |
| Thr: 0.83 | (1) |
| Ser: 1.40 | (3) |
| *Leu: 1.00 | (1) |
| Lys: 0.85 | (1) |
| Pro: 0.88 | (1) |

*standard amino acid
Mass spectrometry (FAB) [M + H]$^+$: 965

EXAMPLE 2

Identification of Antigen Tumor Peptide

HLA-A2402 cDNA (listed in Genbank Accession No. M64740) was obtained from KE-4 in accordance with the description in the publication (*Cancer Res.*, 55:4248, 1995), and a recombinant plasmid was prepared by incorporating the resulting product into an expression vector pCR3 (manufactured by INVITROGEN). This plasmid was transfected to $10^4$ cells of VA-13 cells (available from RIKEN CELL BANK; Ann. Med Exp. Biol. Fenn., 44:242, 1966) by lipofectin method in accordance with the publication (J. Exp. Med., 187:277, 1998), to thereby express HLA-A2402. Each of the peptides "725–733," "740–750," "746–755," "746–756" and "758–766*" among those listed in Example 1 was added at 10 μM in 2 hours, and thereafter the mixture was cultured for 18 hours together with $2\times10^4$ of KE-4CTLs. An amount of IFN-γ produced by KE-4CTLs in the culture supernatant was assayed by ELISA method. Concretely, an anti-human IFN-γ murine monoclonal antibody as a solid-immobilizing antibody was adsorbed to a 96-well plate, and the plate was treated with bovine serum albumin to block nonspecific bonding, and thereafter IFN-γ in the sample was bound to the antibody. Next, an anti-human IFN-γ rabbit polyclonal antibody was bound as a detecting antibody, and an alkaline phosphatase-labeled anti-rabbit immunoglobulin goat antibody (manufactured by Amersham) was further bound thereto. Thereafter, the resulting product was developed by using Peroxidase Developing Kit T (manufactured by Sumitomo Bakelite Company, Limited), and thereafter its absorbance (405 nm) was determined. The resulting value was quantified by comparing it with the value obtained from standard IFN-γ. The results are shown in FIG. 1. In the figure, the abscissa is an amount of IFN-γ (pg/ml) produced by KE-4CTLs. It was clarified from FIG. 1 that these five kinds of peptides function as HLA-A24-restricted tumor antigen peptides.

EXAMPLE 3

Induction of CTLs from Peripheral Blood Lymphocytes by Tumor Antigen Peptide

Whether or not antigen-specific CTLs can be induced from peripheral blood lymphocytes was studied by using peptides "746–755," "746–756" and "758–766*" among those which were shown to function as tumor antigen peptides in Example 2.

First, lymphocytes were isolated by Ficol method from peripheral blood of healthy donors whose HLA-A locus is A24 homo. The lymphocytes were aliquoted to a 24-well plate so as to be $2\times10^6$ cells/well, and cultured in a culture medium containing 45% RPMI 1640 medium, 45% AIM-V medium, 10% FCS and 100 U/ml IL-2. Each of the above-mentioned tumor antigen peptides was added to the culture medium so as to have a concentration of 10 μM, to stimulate the peripheral blood lymphocytes. One week later, the above-mentioned tumor antigen peptide was added thereto so as to have a concentration of 10 μM, together with about $2\times10^5$ of X-ray irradiated (50 Gy) peripheral blood lymphocytes, to carry out a second stimulation of the lymphocytes. After another week, a third stimulation was carried out by repeating the procedures in the same manner as above. After one week from the third stimulation, the cultured lymphocytes were collected. The amount of IFN-γ of the supernatant was assayed by ELISA, the supernatant being produced by reacting the above-mentioned lymphocytes ($8\times10^4$) with HLA-A2402-positive KE-4 cells in which the tumor antigen protein was expressed and with HLA-A2402-negative QG56 cells in which the tumor antigen protein was expressed, respectively, as targeted cells ($1\times10^4$). The results are shown in Table 1.

TABLE 1

| Effector Cells | Target Cells | IFN-γ (pg/ml) in Supernatant |
|---|---|---|
| Peripheral Blood Lymphocytes Stimulated with "746–755" | KE-4 | 595.5 |
|  | QG56 | 281.4 |
| Peripheral Blood Lymphocytes Stimulated with "746–756" | KE-4 | 701.5 |
|  | QG56 | 392.0 |
| Peripheral Blood Lymphocytes Stimulated with "758–766*" | KE-4 | 1121.9 |
|  | QG56 | 537.2 |

From Table 1, while the peripheral blood lymphocytes stimulated with "746–755," "746–756" and "758–766*" exhibited nonspecific reactivities against the negative control QG56, they exhibited stronger reactivities against KE-4. It was shown from this finding that the antigen peptide-specific CTLs were induced.

SEQUENCE LISTING FREE TEXT

The 2nd amino acid in the amino acid sequence of SEQ ID NO: 6 is phenylalanine, tyrosine, methionine or tryptophan, and the 9th amino acid is phenylalanine, leucine, isoleucine, tryptophan or methionine.

The 2nd amino acid in the amino acid sequence of SEQ ID NO: 7 is phenylalanine, tyrosine, methionine or tryptophan, and the 11th amino acid is phenylalanine, leucine, isoleucine, tryptophan or methionine.

The 2nd amino acid in the amino acid sequence of SEQ ID NO: 8 is phenylalanine, tyrosine, methionine or tryptophan, and the 10th amino acid is phenylalanine, leucine, isoleucine, tryptophan or methionine.

The 2nd amino acid in the amino acid sequence of SEQ ID NO: 9 is phenylalanine, tyrosine, methionine or tryptophan, and the 11th amino acid is phenylalanine, leucine, isoleucine, tryptophan or methionine.

The 2nd amino acid in the amino acid sequence of SEQ ID NO: 10 is phenylalanine, tyrosine, methionine or tryptophan, and the 9th amino acid is phenylalanine, leucine, isoleucine, tryptophan or methionine.

INDUSTRIAL APPLICABILITY

According to the present invention, there are provided a tumor antigen peptide derived from SART-1 and a derivative thereof possessing functionally equivalent characteristics thereto; or a therapeutic agent, a prophylactic agent or a diagnostic agent, or the like for tumor, each utilizing these tumor antigen peptide and a derivative thereof in vivo or in vitro. The therapeutic agent or prophylactic agent for tumor of the present invention can be applied to a large number of patients, and the therapeutic agent or prophylactic agent can be widely applied to squamous cell carcinoma, and the like, of which occurrence frequency is high. Therefore, the therapeutic agent or prophylactic agent is expected of utility as an antitumor agent.

What is claimed is:

1. A tumor antigen peptide consisting of SEQ ID NO: 3, wherein said tumor antigen peptide binds to HLA-A24 antigen and is recognized by cytotoxic T cell.

2. A tumor antigen peptide consisting of SEQ ID NO:3, wherein the second amino acid from the N-terminus end is substituted with another amino acid residue selected from the group consisting of: phenylalanine, tyrosine, methionine, and tryptophan, and/or the amino acid at the C-terminus end is substituted with another amino acid residue selected from the group consisting of: phenylalanine, leucine, isoleucine, tryptophan, and methionine, wherein said tumor antigen peptide binds to HLA-A24 antigen and is recognized by cytotoxic T cell.

3. A pharmaceutical composition comprising the tumor antigen peptide of claim 1 or 2 as an active ingredient and a pharmaceutically acceptable carrier.

4. A nucleic acid consisting of a nucleotide sequence which encodes a tumor antigen peptide consisting of SEQ ID NO: 3, wherein said tumor antigen peptide binds to HLA-A24 antigen and is recognized by cytotoxic T cell.

5. A pharmaceutical composition comprising the nucleic acid of claim 4 as an active ingredient.

6. A vector comprising the nucleic acid of claim 4 wherein said vector expresses a tumor antigen peptide consisting of SEQ ID NO: 3.

* * * * *